United States Patent [19]
Dumitriu et al.

[11] Patent Number: 5,858,392
[45] Date of Patent: *Jan. 12, 1999

[54] SUPPORTED POLYIONIC HYDROGELS

[75] Inventors: Severian Dumitriu, Quebec, Canada; Hilda Guttmann, Jerusalem; Itzhak Kahane, Har Adar, both of Israel

[73] Assignees: Yissum Research Development Company of the Hebrew University of Jerusalem; Israel Fiber Institute, State of Israel Ministry & Trade, both of Jerusalem, Israel

[ * ] Notice: The term of this patent shall not extend beyond the expiration date of Pat. No. 5,648,252.

[21] Appl. No.: 806,218

[22] Filed: Feb. 26, 1997

Related U.S. Application Data

[63] Continuation-in-part of Ser. No. 409,264, Mar. 22, 1995, Pat. No. 5,648,252.

[30] Foreign Application Priority Data

Mar. 22, 1994 [IL] Israel ......................................... 109079

[51] Int. Cl.$^6$ .............................. A61K 9/70; C12N 11/12; C12N 11/10; C12N 5/00
[52] U.S. Cl. ........................... 424/443; 435/177; 435/178; 435/179; 435/182; 435/397; 436/529; 436/530; 530/813; 530/814
[58] Field of Search ..................................... 435/179, 177, 435/178, 182, 397; 424/443; 436/529, 530; 530/813, 814

[56] References Cited

U.S. PATENT DOCUMENTS

| | | | |
|---|---|---|---|
| 3,975,350 | 8/1976 | Hudgan et al. ................... | 260/30.41 X |
| 4,452,892 | 6/1984 | Rosevear ................................. | 435/176 |
| 4,578,351 | 3/1986 | Rosevear et al. .......................... | 435/41 |
| 4,744,933 | 5/1988 | Rha et al. ................................. | 264/4.3 |
| 5,116,747 | 5/1992 | Moo-Young et al. ................... | 435/178 |
| 5,648,252 | 7/1997 | Dumitriu et al. ........................ | 435/179 |

*Primary Examiner*—David M. Naff
*Attorney, Agent, or Firm*—Davidson, Davidson & Kappel, LLC

[57] ABSTRACT

A supported polyionic hydrogel is prepared by impregnating a support material with a solution of anionic polysaccharide and a solution of cationic polysaccharide where the anionic polysaccharide and cationic polysaccharide react with each other to form a polyionic hydrogel impregnated in the support material. The hydrogel may be dried such as by lyophilization. Preferably, the anionic polysaccharide is xanthan, dicarboxystarch or dicarboxycellulose and the cationic polysaccharide is chitosan. Especially preferred is a polyionic hydrogel formed from xanthan and chitosan. A paper material or a textile material can be used as the support material. A dry supported polyionic hydrogel can be formed as a bandage without active material incorporated therein. The supported polyionic hydrogel may be formed containing a biologically active material by having the active material in either polysaccharide solution or in another solution impregnated into the support material. The biologically active materials can be enzymes, antibody-producing cells or water-soluble drugs such as the antimicrobial agent, chlorohexidine.

7 Claims, No Drawings

SUPPORTED POLYIONIC HYDROGELS

This application is a continuation-in-part of application Ser. No. 08/409,264, filed Mar. 22, 1995, now U.S. Pat. No. 5,648,252.

The present invention relates to polyionic hydrogels. More particularly, the present invention relates to biocompatible supported polyionic hydrogels which can be used in medicine and biotechnology.

BACKGROUND OF THE INVENTION

Supported hydrogels, as well as hydrogels which act as carriers, are well-known in the art. Thus, e.g., acrylamide-N,N$^1$-methylenebisacrylamide was polymerized in a porous ceramic tube to form a permselective membrane composite useful for separating organic solvents from their water mixtures, as described in Chemical Abstracts, Vol. 113, No. 26, Abstract No. 233075v. In WO 8807075 there is described an enzyme reactor system composed of an enzyme entrapment hydrogel layer coated on a support and an ultraporous thin film membrane diffusion barrier.

In U.S. Pat. No. 4,668,654 there is described a hot or cold compress, comprising a layer of a substituted ureaurethane hydrogel material bonded to one side of a porous substrate, said hydrogel being formed from water, a polyol and a diisocyanate prepolymer. Similarly, in Japanese Patent 57119879, as abstracted in Chemical Abstracts, Vol. 98, No. 4, Abstract No. 1773j, there are described supported or self-supporting hydrogel polymer layers which were prepared using polymeric binders. For example, 2.0 kg ethylene-vinyl acetate copolymer in 8.0 kg PhMe was stirred with 2.0 kg powdered SGP polymer, to give a dispersion which was diluted with PhMe to a viscosity of 5 p and coated on a polyamide non-woven fabric.

SUMMARY OF THE INVENTION

In contradistinction, however, to said prior art supported hydrogels, the present invention provides a dry supported polyionic hydrogel, formed by impregnating a support material with an anionic polysaccharide and a cationic polysaccharide in solution, whereby said anionic polysaccharide and said cationic polysaccharide react with each other while in contact with and impregnated into said support material to form a polyionic hydrogel, and drying the hydrogel, and wherein said support material is suitable for impregnation by said polysaccharides in solution.

More particularly, the present invention provides a supported polyionic hydrogel formed by impregnating a support material with a solution of an anionic polysaccharide and a solution of a cationic polysaccharide, whereby said anionic polysaccharide and said cationic polysaccharide react with each other while in contact with and impregnated into said support; wherein said support material is suitable for impregnation by said solutions and is selected from the group consisting of a stable woven material, a non-woven material, a knitted material, a natural polymer material, a synthetic polymer material, and combinations thereof, and wherein said anionic polysaccharide is selected from the group consisting of xanthan, dicarboxystarch, and dicarboxycellulose, and said cationic polysaccharide is chitosan.

Especially preferred is a supported polyionic hydrogel formed by the interaction between xanthan and chitosan.

In U.S. Pat. No. 4,452,892 there is disclosed the application of a gel precursor which contains a biologically active material onto a support material, followed by a polymerization of the gel precursor to form a supported biologically active, material-containing hydrogel. Similarly, U.S. Pat. No. 4,578,351 discloses the production of chemical compounds with immobilized plant cells.

In U.S. Pat. No. 4,744,933, there is disclosed the encapsulation of an active material within a membrane formed by the reaction of an anionic polymer such as xanthan with a cationic polymer such as chitosan.

U.S. Pat. No. 5,116,747 discloses the immobilization of a biologically active material within the pores of a fibrous chitosan-alginate matrix.

None of said patents, however, teaches or suggests the supported hydrogels of the present invention as defined and exemplified herein.

As will be realized, the prior art hydrogels were first formed and then coated onto a supporting fabric or film, while in the present invention the hydrogel is itself formed while in contact with a cellulose or synthetic fibre or a mixture thereof, or while in contact with a natural or synthetic polymer or a combination thereof, to form a fiber, fabric, sheet, or other stable woven, non-woven, or knitted material having said polyionic hydrogel incorporated therein.

Furthermore, it has now been surprisingly found that the supported hydrogels of the present invention can be used as a bandage without any active material incorporated therein, and that such bandages exhibit improved microbiology, reduced contamination and healing properties when compared with standard gauze pads, as shown in Example 5 hereinafter.

DETAILED DESCRIPTION OF THE INVENTION

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

Impregnation of Woven Cotton Fabric with Hydrogel and Antimicrobial Agents

Pieces of woven cotton fabric were impregnated with hydrogel and antimicrobial agents by immersing them in 10 ml of various solutions (0.1% xanthan, 0.3% chitosan, 0.2% chlorohexidine gluconate, or 1% iodine ($I_2$+KI). The schedule of sequence of impregnation is outlined in Table 1 below. The incubation in the xanthan solution was for 5 min, except for 10 min for samples 7 and 8. In the chitosan solution, it was 10 min, with no exceptions. The length of incubation in the chlorohexidine solution was 3 or 5 min, and in the $I_2$+KI solution, 5 or 10 min; all are indicated in Table 1. At the end of an incubation period, the excess solution was removed by squeezing of the fabric, and the sample was weighed and transferred to the next incubation step. The WPU and DPN of the various samples is outlined in Table 1.

The antimicrobial activities of the various samples were assessed as follows: The antimicrobial activity of the product was tested on lawns of several bacteria: *Staphylococcun aureus* (SA); *S. epidermidis* (SE); *Escherichia coli* (EC); and *Pseudonomas aeruginosa* (PA), inoculated on agar plates by placing a sample of about 2 cm$^2$ on the surface of the plate and measurements of the inhibition zone after growth of the bacteria for 18 hours at 37° C. The results are summarized in Table 2.

The data in Table 1 and hereinafter are presented as follows:
(a) no inhibition
(x–y) growth inhibition in mm.
x=minimum distance
y=maximum distance containing a mixture of xanthan and urease (10 ml 0.3% xanthan+100 ml urease). The excess xanthan-urease solution was removed by squeezing. The wet pick-up for the paper and cotton was about 126% and 132%, respectively. The samples were immersed for 10 min in a solution of 0.3% chitosan, pH 6.4. The samples were then squeezed again. The wet pick-up was about 128% for both samples. The samples were dried at room temperature.

The urease activity in the hydrogel urease system was determined by measuring the release of ammonia from the urea, as detected by a modified Berthelots reaction. This was conducted as follows: weighed samples of paper and cotton impregnated with the hydrogel-urease system, as described above, were immersed for 15 min in a vessel containing 500 ml of 50 mM urea in HED buffer [50 mM N-2-hydroxyethylpiperazine tetraacetic acid, 3 mM ethylenediamine-tetraacetic acid, 1 mM dithiothreitol (Sigma Chemicals, Israel)], pH 7.0, and then 1 ml of 25 mM NaOH was added to the reactor. Samples of 100 ml were

TABLE 1

Impregnation of Woven Cotton Fabric with Hydrogels and Drugs

| Sample # | Treatment Schedule 1 | 2 | 3 | Xanthan WPU % | Chitosan WPU % | Chlorohexidine min. | Chlorohexidine WPU % | Xanthan + I$_2$ min. | Xanthan + I$_2$ WPU % | I$_2$ min. | I$_2$ WPU % | DPU % |
|---|---|---|---|---|---|---|---|---|---|---|---|---|
| 1 | XA | CHI | — | 119.6 | 123.5 | — | — | — | — | — | — | 9.5 9.1 |
| 2 | CHI | I$_2$ | — | — | 129.7 | — | — | — | — | x/10 | 146.6 | 29.17 28.07 |
| 3 | CHX | XA | CHI | 124.9 | 118.9 | x/3 | 133.8 | — | — | — | — | 10.5 9.8 |
| 4 | XA | CHX | CHI | 123.22 | 126.2 | x/5 | 130.2 | — | — | — | — | 11.6 |
| 5 | XA | I$_2$ | CHI | 126.0 | 121.2 | — | — | — | — | x/5 | 146.7 | 14.7 |
| 6 | XA | I$_2$ | CHI | — | 123.9 | — | — | x/10 | 119.2 | — | — | 11.5 10.8 |
| 7* | XA | CHX | — | 137.4 | — | x/5 | 149.7 | — | — | — | 11.9 | 3.5 |
| 8* | CHX | XA | — | 166.6 | — | x/5 | 164.4 | — | — | — | 16.8 | — |

*= drip drying
WPU = wet pickup, DPU = dry pickup
xanthan = XA; chitosan = CHI; chlorohexidine = CHX; I$_2$ + KI = I$_2$ It is indicated in Table 2 that antimicrobial agents can be included in the hydrogel, and that the sequence of impregnation was important.

TABLE 2

Antimicrobial Activity of Woven Cotton Fabric Impregnated with Hydrogels and Antimicrobial Agents

| Sample* | SA | EC | PA | SE |
|---|---|---|---|---|
| 1 | a | a | a | a |
| 2 | 4–5 | 3–5 | 2–3 | 5–8 |
| 3 | 3–4 | 2–4 | 0–1 | 3–4 |
| 4 | 3–4 | 3–4 | 1–2 | 3–4 |
| 5 | 0–1 | 0–4 | a | 0–1 |
| 6 | 24 | 2–3 | 1–2 | 2–3 |
| 7 | 3–5 | 3–5 | 2–4 | 4–7 |
| 8 | 3–4 | 3–4 | 2–3 | 4–5 |

*The sample impregnation is described in Table 1.

EXAMPLE 2

The Inclusion of the Hydrogel Urease System into Paper and Woven Cotton Fabric

In the first step, a piece of filter paper and a piece of woven cotton fabric were immersed for 10 min in a solution withdrawn in order to measure the amount of ammonia released from urea, using the Berthelots reaction. Absorbance of the reaction mixtures was measured spectrophotometrically at 625 nm.

Most of the enzyme was included in the hydrogel, as only about 5% of its activity was detected in the xanthan urease solution at the end of the first step. The enzymic activity was measured in the hydrogel on support after storage for one day or two weeks, with only about 30% loss (Table 2).

As seen in Table 3, about 70% of the urease activity was detected even after two weeks' storage of the hydrogel, on both paper and cotton supports. Comparable results were found for the urease activity on the xanthan-chitosan hydrogel without the support, as described below in Example 3.

EXAMPLE 3

Immobilization of Urease in Hydrogel

Urease (300 ml) in HED buffer was added to 30 ml of 0.3% xanthan and stirred. Then 30 ml of the 0.3% chitosan solution, at pH 6.4, were added. The gel formed was stirred for 15 min at room temperature. The mixture was centrifuged for 15 min at 15,000 rpm. The supernatant was removed and the gel washed with 2 ml of the HED buffer. The gel was separated by centrifugation and was lyophilized and stored at −20° C. The urease activity in the hydrogel was assayed as described above in Example 2, and the results are summarized in Table 3. The urease also retained its activity in this hydrogel after lyophilization and rehydration.

TABLE 3

Activity of Hydrogel Urease System

| Sample | Urease Activity (%) |
|---|---|
| Hydrogel on paper (after 1 day) | 100 |
| Hydrogel on paper (after 2 weeks) | 68 |
| Hydrogel on cotton (after 1 day) | 100 |
| Hydrogel on cotton (after 2 weeks) | 70 |
| Hydrogel by itself | 100 |
| Hydrogel by itself (after 1 day) | 84 |
| Hydrogel by itself (after 2 weeks) | 68 |
| Hydrogel lyophylized | 1.472 |

EXAMPLE 4

Inclusion of Cells in Hydrogels

A suspension of monoclonal antibody-producing cells, containing $10^5$/ml cells, was centrifuged for 5 min at 15,000 rpm. The cells were suspended in 10% FCS+DMEM. A solution of 0.3% xanthan and a solution of 0.3% chitosan at pH 4.2 were separately sterilized for 1.5 h. The solution of chitosan was neutralized under sterile conditions with sterile (filtered) 1.5% $NaHCO_3$ until the pH reached the value of 6.2–6.4 (by pH paper). 18 ml of the cell suspension in DMEM were added to the 20 ml solution of 0.3% xanthan. Then 20 ml of a solution of 0.3% chitosan was added and stirred. The gel formed was separated when the supernatant was aspirated, and 50 ml fresh DMEM at 37° C. was added. The cells were incubated in 5% $CO_2$+air at 37° C. Samples were drawn after 24 h and 72 h, and tested for MAb production.

TABLE 4

Monoclonal Antibody Production by Cells in Hydrogel

| | CPM |
|---|---|
| Medium | 300 |
| Cells 24 h | 610 |
| Cells 72 h | 920 |

MAb was assessed by radioimmunoassay.

As seen above in Table 4, the cells continued to produce the monoclonal antibodies for at least 4 days after inclusion in the hydrogel.

EXAMPLE 5

Pieces of woven cotton fabric were impregnated with hydrogel by immersing them in 10 ml of solutions of 0.1% xanthan and 0.3% chitosan, wherein the schedule of sequence of impregnation was as outlined above in Example 1. Bandages formed from said fabric, having no antimicrobial agents incorporated therein, were applied to guinea pigs, as were standard sterile gauze dressings.

a) The microbiology of contamination grade (expressed in %) of *S. aureus* in a 2 cm standard straight wound treated by wet dressings is set forth in Table 5A hereinafter, wherein each dressing was treated with 2 ml of 0.9 sterile saline once a day and each dressing was changed every 3 days.

TABLE 5A

| Day | cfu | Gauze (control) | Hydrogel clear |
|---|---|---|---|
| Day 3 | 0 | 6.9% | 0.0% |
| | $1 \times 10 - 1 \times 10^2$ | 13.8% | 76.9% |
| | $1 \times 10^3 - 1 \times 10^5$ | 10.3% | 15.4% |
| | $>1 \times 10^5$ | 69.0% | 7.7% |
| Day 6 | 0 | 0.0% | 23.1% |
| | $1 \times 10 - 1 \times 10^2$ | 5.9% | 61.5% |
| | $1 \times 10^3 - 1 \times 10^5$ | 52.9% | 15.4% |
| | $>1 \times 10^5$ | 41.2% | 0.0% |

In the above Table, the following grading was used, based on observation of the cultures:

| CFU | Grading |
|---|---|
| 0 | 0 |
| $1 \times 10 - 1 \times 10^2$ | 1 |
| $1 \times 10^3 - 1 \times 10^5$ | 3 |
| $>1 \times 10^6$ | 5 | b) Contamination grade in a 2 cm straight wound contaminated by *S. aureus* after treatment with several wet dressings. Each dressing was treated with 2 ml of 0.9% sterile saline once a day and each dressing was changed every 3 days. The results are set forth in Table 5B:

TABLE 5B

| Day | Gauze (control) | Hydrogel clear |
|---|---|---|
| Day 3 | (n = 29) | (n = 13) |
| | 3.90 ± 1.80 | 1.61 ± 1.21 |
| Day 6 | (n = 17) | (n = 13) |
| | 3.71 ± 1.21 | 1.08 ± 0.92 |

Data includes mean ± standard deviation.

c) Tensile strength (expressed in grams) needed to separate a 2 cm standard straight contaminated by *S. aureus* after treatment with several wet dressings is set forth in Table 5C. Each dressing was treated with 2 ml of 0.9% sterile saline once a day and was changed every 3 days.

TABLE 5C

| Day | Gauze (control) | Hydrogel clear |
|---|---|---|
| Day 3 | (n = 15) | (n = 13) |
| | 87 ± 36[a] | 128 ± 31[b] |
| Day 6 | (n = 13) | (n = 13) |
| | 197 ± 119 | 239 ± 85 |

Data includes ± standard deviation.

a ↔ b (T-test) p<0.004 d) Percentage of healed area (expressed in %) compared to the initial wound area, in a 2 cm straight wound contaminated by *S. aureus* after treatment with several wet dressings is set forth in Table 5D. Each dressing was treated with 2 ml of 0.9% sterile saline once a day and each dressing was changed every 3 days.

TABLE 5D

| Day | Gauze (control) | Hydrogel clear |
|---|---|---|
| Day 3 | (n = 30) | (n = 13) |
|  | 61.6 ± 6.8 | 68 ± 13.2 |
| Day 6 | (n = 17) | (n = 13) |
|  | 66.7 ± 5.9$^a$ | 78.4 ± 9.5$^b$ |

Data includes ± standard deviation.
a ↔ b (T-test) p<0.02

What is claimed is:

1. A supported polyionic hydrogel formed by impregnating a support material with a solution of an anionic polysaccharide selected from the group consisting of xanthan, dicarboxystarch and dicarboxycellulose, and a solution of chitosan, whereby said anionic polysaccharide and said chitosan react with each other while in contact with and impregnated into said support material:

wherein said support material is suitable for impregnation by said solutions, said support material being selected from the group consisting of a stable woven material, a non-woven material, a knitted material, a natural polymer material, a synthetic polymer material, and combinations thereof.

2. The supported polyionic hydrogel according to claim 1, wherein said polyionic hydrogel is dehydrated.

3. The supported polyionic hydrogel according to claim 1, wherein said support material is selected from the group consisting of a paper material and a textile material.

4. A supported polyionic hydrogel, formed by a method comprising the steps of:

impregnating into a porous support material a solution of an anionic polysaccharide selected from the group consisting of xanthan, dicarboxystarch and dicarboxycellulose, and impregnating a chitosan solution into said porous support material, whereby said anionic polysaccharide and said chitosan react with each other while in contact with and impregnated into said porous support material, to produce a polyionic hydrogel impregnated into said porous support material.

5. A dry supported polyionic hydrogel, said hydrogel formed by the process of impregnating a support material with an anionic polysaccharide selected from the group consisting of xanthan, dicarboxystarch and dicarboxycellulose, and chitosan in solution, whereby said anionic polysaccharide and said chitosan react with each other while in contact with and impregnated into said support material to form a polyionic hydrogel, and drying the hydrogel, wherein said support material is suitable for impregnation by anionic polysaccharides and said chitosan in solution.

6. A supported hydrogel according to claim 5, wherein said support material is selected from the group consisting of a paper material and a textile material.

7. A dry supported polyionic hydrogel according to claim 5, in the form of a bandage and substantially free of any active ingredient.

* * * * *